(12) United States Patent
Nakamura et al.

(10) Patent No.: US 6,359,176 B1
(45) Date of Patent: Mar. 19, 2002

(54) CATIONIC SURFACTANTS, PROCESS FOR PRODUCING THE SAME AND UTILIZATION THEREOF

(75) Inventors: Masaki Nakamura, Takatsuki; Jia-he Qian, Yao; Hiromitsu Seike, Yao; Takeshi Munekiyo, Yao, all of (JP)

(73) Assignees: Matsumoto Yushi-Seiyaku Co., Ltd.; Saka City Government, both of Osaka (JP)

( * ) Notice: Subject to any disclaimer, the term of this patent is extended or adjusted under 35 U.S.C. 154(b) by 0 days.

(21) Appl. No.: 09/582,869

(22) PCT Filed: Jan. 12, 1999

(86) PCT No.: PCT/JP99/00071

§ 371 Date: Jul. 6, 2000

§ 102(e) Date: Jul. 6, 2000

(87) PCT Pub. No.: WO99/36167

PCT Pub. Date: Jul. 22, 1999

(30) Foreign Application Priority Data

Jan. 13, 1999 (JP) ............................... 10-018274

(51) Int. Cl.$^7$ ............................................. C07C 211/63
(52) U.S. Cl. ........................................ 564/292; 560/129
(58) Field of Search ........................................... 564/292

(56) References Cited

U.S. PATENT DOCUMENTS

| | | | |
|---|---|---|---|
| 2,060,850 A | * | 11/1936 | Calcott ..................... 260/127 |
| 3,855,290 A | | 12/1974 | Zak et al. |
| 5,399,272 A | | 3/1995 | Swartley et al. |

FOREIGN PATENT DOCUMENTS

| | | | |
|---|---|---|---|
| DE | 4238211 | | 11/1997 |
| JP | 5019719 | | 3/1975 |
| JP | 59142299 | | 8/1984 |
| JP | 1280078 | | 11/1989 |
| JP | 05148288 | * | 6/1993 |
| JP | 6316869 | | 11/1994 |
| JP | 7229061 | | 8/1995 |

OTHER PUBLICATIONS

Veksler, V.I. et al, "Surfactants based on N–methyl–D–glucamine", Zh. Obshch. Khim. (1980), 50(9), 2120–3.*

Veksler, V.I. et al, "D–sorbitol derivatives as cationic surfactants", Zh. Obshch. Khim. (1974), 44(10), 2367–8.*

Veksler, V.I. et al, "Synthesis of antimicrobial substances–derivatives of D–sorbitol", Zh Obshch. Khim., Zh. Obshch. khim. (1979), 49(12), 2731–8.*

* cited by examiner

Primary Examiner—Gary Geist
Assistant Examiner—John N. Calve

(57) ABSTRACT

The present invention provides cationic surfactants derived from the amino derivatives of hexose alcohol, a reduced alcohol of hexose or reduced sugar of glucose, which is produced by converting 1-amino-hexose alcohol into a quaternary salt and by esterifying with fatty acid. The cationic surfactants have superior biodegradability.

14 Claims, No Drawings

US 6,359,176 B1

CATIONIC SURFACTANTS, PROCESS FOR PRODUCING THE SAME AND UTILIZATION THEREOF

TECHNICAL FIELD

The present invention relates to cationic surfactants, process for producing the same and utilization thereof. Specifically novel cationic surfactants of high biodegradability derived from hexose, process for producing the same and utilization thereof.

PRIOR ART

Cationic surfactants have been used as a softener for textiles, rinse for shampoo and hair treatment, or a bactericide. Those cationic surfactants contain quaternary ammonium salt and thus their poor biodegradability has been a serious disadvantage. Among those, alkyl trimethyl ammonium chlorides and dialkyl dimethyl ammonium chlorides that have been popular surfactants are being regulated in Europe, especially in Netherlands, because of their low biodegradability. The regulation in Europe has been advancing toward the use of the compounds having at least one ester, a decomposable group, in their molecular structure. Under such social condition, developing more biodegradable cationic surfactants is an utmost need not only from the viewpoint of safety (non-toxic to skin etc.) but also from the viewpoint of environmental protection.

Although the conventional development trend of cationic surfactants has been concentrated on the surfactants having a molecular structure in which esters are introduced into alkyl chains, it is more advantageous to develop compounds derived from natural sugars for meeting the current trend toward surfactants of higher biodegradability. The inventors of the present invention investigated on deriving cationic surfactants from the amine derivatives of reducing sugar of glucose or the amine derivatives of hexose alcohols that are reducing alcohol of hexose. As the result, the inventors found the cationic compound of superior biodegradability produced by esterifying a quaternary salt, which is a derivative of 1-amino-hexose alcohol produced by the reaction (reductive amination) of glucose or other hexose (a reducing sugar) with ammonia or primary amines, with a fatty acid.

DISCLOSURE OF INVENTION

The object of the present invention is to provide highly biodegradable new cationic surfactants produced from natural raw materials.

Another object of the present invention is to provide a profitable industrial process for producing the above cationic surfactants of the present invention.

Further object of the present invention is to provide fiber being treated with the above cationic surfactant of the present invention and having superior water absorptiveness and antistaticity and low friction.

Yet further object and advantage of the present invention are illustrated in the following description.

The above object and advantage of the present invention are, first, achieved by a cationic surfactant represented by the following formula (1),

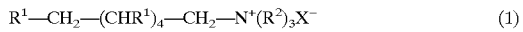

wherein five $R^1$s are hydroxyls or their esters independently to each other, three $R^2$s are hydrocarbons having 1 to 6 carbon atoms and can contain hydroxyls or esters independently to each other, $X^-$ is an anion of halogen atoms, hydrogen sulfate or organic acid, and at least one of the five $R^1$s is an ester.

The above object and advantage of the present invention are, secondly, achieved by a process for producing cationic surfactant (hereinafter referred to as the first production process of the present invention), wherein a cationic surfactant represented by the above-mentioned formula (1) is produced through the following steps, (A) reacting 1-amino hexose alcohol represented by the following formula (2)

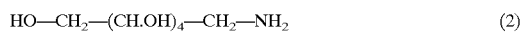

with a halide represented by the following formula (3)

wherein $R^2$ and X are the same as defined in the above formula (1) to produce an ammonium salt of N-hydrocarbon-1-amino hexose alcohol represented by the following formula (4)

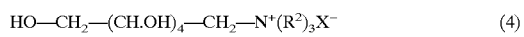

wherein $R^2$ and X are the same as defined in the above formula (1); and (B) reacting the above ammonium salt of N-hydrocarbon-1-amino hexose alcohol with an acid halide.

And the above object and advantage of the present invention are, thirdly, achieved by a process for producing cationic surfactant (hereinafter referred to as the second production process of the present invention), wherein a cationic surfactant represented by the above-mentioned formula (1) is produced through the following steps, (A) reacting 1-amino hexose alcohol represented by the above formula (2) with a halide represented by the above formula (3) to produce an ammonium salt of N-hydrocarbon-1-amino hexose alcohol represented by the above formula (4); and (B') reacting the above ammonium salt of N-hydrocarbon-1-amino hexose alcohol with an organic acid in dehydration condensation.

Further the above object and advantage of the present invention are, fourthly, achieved by a process for producing cationic surfactant (hereinafter referred to as the third production process of the present invention), wherein a cationic surfactant represented by the above-mentioned formula (1) of which one of the three $R^2$s is a methyl and other two are hydrocarbons that can contain hydroxyls or esters is produced through the following steps, (A') reacting N-methyl glucamine represented by the following formula (5)

with a halide represented by the above formula (3) to produce an ammonium salt of N-hydrocarbon-1-amino hexose alcohol represented by the above formula (4) of which one of the three $R^2$s is a methyl and other two are hydrocarbons that can contain hydroxyls or esters; and (B") reacting the above ammonium salt of N-hydrocarbon-1-amino hexose alcohol with an acid halide.

Finally the above object and advantage of the present invention are achieved with the textile treated with the above cationic surfactants of the present invention.

PREFERRED EMBODIMENT OF INVENTION

The cationic surfactants of the present invention are represented by the above formula (1), wherein each of five $R^1$s is a hydroxyl (—OH) or its ester independently to each other. The ester is represented by the formula, RCOO—; in which R is preferably a straight or branched chain and saturated or unsaturated hydrocarbon having 5 to 28 carbon atoms and may contain aromatics. The examples of such hydrocarbon are alkyls, such as pentyl, hexyl, heptyl, octyl, nonyl, decyl, lauryl, myristyl, cetyl, stearyl, eicosanyl and hexacosanyl; and their correspondent alkenyls, such as pentenyl and hexenyl.

Each of the three $R^2$s in formula (1) is a hydrocarbon having 1 to 6 carbon atoms and may contain hydroxyls or esters independently. The hydrocarbon having 1 to 6 carbon atoms may be straight or branched chain and saturated or unsaturated. The examples of such hydrocarbon are alkyls, such as methyl, ethyl, propyl, butyl, pentyl and hexyl, and correspondent alkenyl or alkynyls having 2 to 6 carbon atoms.

The $X^-$ is an anion of halogen atoms, hydrogen sulfate ($HSO_4^-$) or organic acids ($RCOO^-$). The examples of preferable halogen anions are fluorine anion, chlorine anion, bromine anion and iodine anion. The examples of preferable anions of organic acids are those having 2 to 12 carbon atoms, i.e., monobasic acid anions, such as acetic acid an ion and propionic acid anion; dibasic acid anions, such as oxalic acid and malonic acid; and anions of oxyacid, such as citric acid and malic acid.

At least one of the five $R^1$s of the cationic surfactant represented by the above formula (1) must be an ester, such as monoesters, di-esters, trimesters, tetra-esters and penta-esters.

Among the compounds represented by the above formula (1), the compound of which all of three $R^2$s in formula (1) are methyls as represented by the following formula (6),

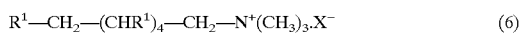

$$R^1—CH_2—(CHR^1)_4—CH_2—N^+(CH_3)_3.X^- \quad (6)$$

wherein $R^1$ and $X^-$ are the same as defined in the above formula (1), is preferable because of its superior biodegradability to that of others.

The cationic surfactants of the present invention represented by the above formula (1) are preferably produced in the above first, second and third production processes of the present invention.

The step (A) of the first production process produces the ammonium salt of N-hydrocarbon-1-amino hexose alcohol represented by the formula (4) by reacting 1-amino hexose alcohol represented by the formula (2) and a halide represented by the formula (3).

The examples of the halides represented by the formula (2) are the chlorides, bromides and iodides of alkyl, alkenyl and alkynyls having 1 to 6 carbon atoms.

Then the step (B) produces the cationic surfactants represented by the formula (1) by reacting the above product in the step (A) with an acid halide ($RCOX^1$).

The reaction occurs between the hydroxyls (—OH) of the product in the step (A) and acid halide ($RCOX^1$) to produce esters (RCOO—). The esters (RCOO—) are the $R^1$s, which represent esters in the formula (1).

The examples of the above acid halides are saturated fatty acid halides, such as caproyl halide, capriroyl halide, capryl halide, lauroyl halide, miristoyl halide, palmitoyl halide and stearoyl halide; and unsaturated fatty acid halides correspondent to them.

The steps (A) and (B) are known reaction processes, the reaction of aminos into quaternary compounds and esterification.

The second production process of the present invention consists of the step (A), which is the same as the step (A) of the first production process, and the step (B') which produces the cationic surfactants represented by the formula (1) by reacting the product in the step (A) with an organic acid in dehydration condensation.

The organic acids are represented by RCOOH. And the examples of such acids are saturated fatty acids, such as caproic acid, enanthic acid, caprylic acid, capric acid, lauric acid, myristic acid, palmitic acid, stearic acid, behenic acid and montanic acid; and their correspondent unsaturated fatty acids.

The product can be dehydrated by heating with acidic catalysts, such as sulfuric acid, paratoluene sulfonic acid, hydrochloric acid and resins of high acidity.

In the third production process, the step (A') produces the compound represented by the formula, $HO—CH_2—(CH.OH)_4—CH_2—N^+(CH_3)(R^2)_2X^-$, wherein $R_2$ and $X^-$ are the same as defined in the above formula, i.e., the ammonium salt of N-hydrocarbon-1-amino hexose alcohol represented by the above formula (4) wherein one of the three $R^2$s is a methyl and other two are hydrocarbons that can contain hydroxyls or esters by reacting N-methyl glucamine represented by the formula (5) with a halide represented by the formula (3).

The step (B") reacts the product in the step (A') with an acid halide to produce a cationic surfactant represented by the above formula (1) wherein one of the three $R^2$s is a methyl and other two are hydrocarbons that can contain hydroxyls or esters. In this step, the preferable temperature and time for the reaction to produce monoesters, diesters or triesters with an acid halide, such as fatty acid halide having 12 to 18 carbon atoms, are several degrees, such as five degrees, in Celsius and several hours, such as 3 to 6 hours.

The cationic surfactants of the present invention or their mixture with conventional cationic surfactants can impart softness and antistaticity to textile yarns and fabrics and decrease the friction on their surface with known application process (usually applying with absorption or padding to 0.005 to 3 weight percent of fiber weight.). The hair-caring toiletries, such as rinse or treatment produced by adding the cationic surfactants to known oil ingredients, such as vegetable oils or liquid paraffin, function similarly to impart similar effect (usually at 1 to 5% of hair weight) to hair.

EXAMPLES

The present invention is specifically illustrated with the following examples.

Example 1

(A) Reaction of producing quaternary N-methyl glucamine

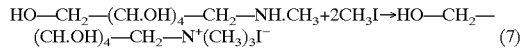

$$HO—CH_2—(CH.OH)_4—CH_2—NH.CH_3+2CH_3I \rightarrow HO—CH_2—(CH.OH)_4—CH_2—N^+(CH_3)_3I^- \quad (7)$$

(A1) Reaction parameters and procedure
The parameters for the synthesis are as follows.

| | | |
|---|---|---|
| (1) N-methyl glucamine (MW = 195.22) | 7.81 g (0.04 mol) |
| (2) Methyl iodide (MW = 141.94) | 57 g (0.40 mol) |

| | |
|---|---|
| (3) Methanol | 40 ml |
| (4) Sodium carbonate (MW = 106) | 21.2 g (0.2 mol) |
| (5) Temperature (° C.) | 50–55 |
| (6) Time (hour) | 12–24 |

A cooling tube equipped with a silica-gel drying tube was attached to a 300-ml flask. The above chemicals were placed in the flask and reacted under the above-mentioned condition. The quantity of the methyl iodide can be decreased to 2.5 to 3 times of the equivalent to the quantity of methyl glucamine when cold water is used for cooling.

(A2) Refining

After the reaction, approx. 200 ml of methanol was placed in the flask and treated at the same temperature for 30 minutes. Then the reaction product was filtered through filter paper to remove inorganic substances, such as sodium carboxylate. The filtration was condensed with a rotary evaporator to remove the solvent and remained methyl iodide that was added excessively, and approx. 15 g of crude substance (100% yield) was obtained. The crude substance was dissolved with approx. 500 ml of ethanol and filtered through filter paper to remove remained inorganic salts.

The above crude substance was dissolved with approx. 400 ml of ethanol and re-crystallized. Approx. 10 to 11 g of refined substance (72 to 79-% re-crystallization yield) was obtained.

(A3) Analysis with IR Spectrum

| | |
|---|---|
| 2960, 2855 cm$^{-1}$ | —$CH_3$, —$CH_2$— |
| 1477 cm$^{-1}$ | —$CH_3$, —$CH_2$— |
| 1082 cm$^{-1}$ | —C—O— |
| 970, 920 cm$^{-1}$ | —C—N— |
| 3430 cm$^{-1}$ | —OH |

$^1$H NMR Spectrum analysis (solvent: heavy water, 300MH$_z$ -NMR)

HO—$CH_2$—$(CH.OH)_4$—$CH_2$—$N^+(CH_3)_3I^-${6H}{2H}{9H}

(3.5–3.9 ppm and 4.38 ppm)(3.55 ppm)(9H 3.22 ppm)

(B) Synthesis of derivatives of monolaurate

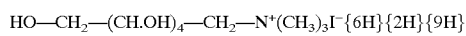
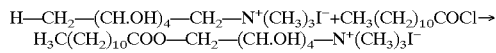

(B1) Synthesizing parameters and procedure

The synthesis was carried out under the following condition.

(1) Quaternary salt of N-methyl glucamine (7) (MW=351.2): 500 mg (1.42 mM, 1 eq.)
(2) $C_{12}H_{25}COCl$ (MW=218.77): 405 mg (1.85 mM, 1.3 eq.)
(3) Pyridine anhydride and DMF anhydride: 3 ml+5 ml
(4) Temperature (° C.): room temperature (approx. 25° C.)
(5) Time (hr): 4
(6) Yield (%, after isolated in column chromatography): 59

The quaternary salt was placed in a 50-ml round-bottomed flask and pyridine anhydride and DMF anhydride was added. After dissolving them, lauroyl chloride was quickly added and agitated well to react with cutting out the moisture in the air.

(B2) Refining

After the reaction, 5 ml of ethanol was added and agitated for 30 minutes, and the solvent was removed with a rotary evaporator.

The reacted substance was isolated from the remained substance in column chromatography with the mixture of methanol/ethyl acetate (20–100:80–0 in vol %) as the solvent.

(C1) Analysis with IR spectrum

| | |
|---|---|
| 2957, 2924, 2855 cm$^{-1}$ | —$CH_3$, —$CH_2$ |
| 1468 cm$^{-1}$ | —$CH_3$, —$CH_2$ |
| 1379 cm$^{-1}$ | —$CH_3$ |
| 721 cm$^{-1}$ | —$(CH_2)_n$— |
| 1726 cm$^{-1}$ | —CO—O— |
| 3430, 1084 cm$^{-1}$ | —CH, —C—O— |
| 970, 920 cm$^{-1}$ | —C—N— |

(C2) The resultant substance was identified as a derivative of monolaurate with $^1$H NMR spectrum analysis (solvent: heavy water, 300 MH$_z$-NMR) as shown below. The anion was identified as Cl$^-$ with ion chromatography.

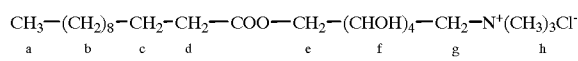

a (3H, 0.83 ppm), b (16H, 1.25 ppm), c (2H, 1.58 ppm), d (2H, 2.37 ppm), e (2H, 4.36 ppm), f (4H, 3.7–4.1 ppm), g (2H, 3.55 ppm), h (9H, 3.20 ppm)

Example 2

A derivative of monomyristate was synthesized in 47% yield with the same apparatus, procedure and refining as in Example 1 under the following synthesizing condition.

(1) Quaternary salt of N-methyl glucamine (MW=351.2): 500 mg (1.42 mM, 1 eq.)
(2) Myristyl chloride (MW=246.82): 457 mg (1.85 mM, 1.3 eq.)
(3) Pyridine anhydride and DMF anhydride: 2 ml+3 ml
(4) Temperature and time: room temperature for 4 hr, and 50° C. for 2 hr
(5) Yield per mol (%, after isolation): 47

Analysis with IR spectrum

| | |
|---|---|
| 2957, 2924, 2855 cm$^{-1}$ | —$CH_3$, —$CH_2$ |
| 1468 cm$^{-1}$ | —$CH_3$, —$CH_2$ |
| 1724 cm$^{-1}$ | —CO—O— |
| 3430, 1086 cm$^{-1}$ | —OH, —C—O— |
| 972, 922 cm$^{-1}$ | —C—N— |

The structure of the resultant derivative of monomyristate was analyzed with $^1$H NMR spectrum analysis as shown below.

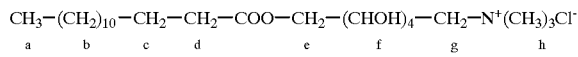

a (3H, 0.83 ppm), b (20H, 1.25 ppm), c (2H, 1.57 ppm), d (2H, 2.37 ppm), e (2H, 4.34 ppm), f (4H, 3.65–4.14 ppm), g (2H, 3.53 ppm), h (9H, 3.20 ppm)

Example 3

A derivative of monopalmitate, i.e. a monoester, was synthesized in 61% yield in the same manner as in Example 2 except replacing myristyl chloride with 509 mg (1.85 mM, 1.3 eq.) of palmitoyl chloride (MW=274.88).

Example 4

A derivative of monostearate, i.e. a monoester, was synthesized in 65% yield in the same manner as in Example 2 at room temperature to 60° C. for 13 hours except using 561 mg (1.85 mM, 1.3 eq.) of stearoyl chloride (MW=302.93).

Example 5

A derivative of laurate, i.e. a mixture of triester and diester, was synthesized in the same manner as in Example 1 at room temperature to 80° C. for 14 hours except using 0.748 g (3.42 mM, 2.4 eq.) of lauryl chloride (MW=218.77).
Refining After the reaction, 5 ml of ethanol was added and agitated for 30 minutes. After removing the solvent completely with a rotary evaporator, the resultant substance was separated with column chromatography to isolate the triester and diester. The triester derivative was obtained in 660 mg and the diester derivative was obtained in 345 mg.
IR Spectrum Analysis
Dilaurate Derivative

| | |
|---|---|
| 2957, 2920, 2853 $cm^{-1}$ | —$CH_3$, —$CH_2$ |
| 1468 $cm^{-1}$ | —$CH_3$, —$CH_2$ |
| 1379 $cm^{-1}$ | —$CH_3$ |
| 1738 $cm^{-1}$ | —CO—O— |
| 3430, 1076 $cm^{-1}$ | —OH, —C—O— |
| 968, 920 $cm^{-1}$ | —C—N— |
| 722 $cm^{-1}$ | —$(CH_2)_n$—, higher absorption than monolaurate derivative |

| Trilaurate derivative | |
|---|---|
| 2955, 2919, 2851 $cm^{-1}$ | —$CH_3$, —$CH_2$ |
| 1468 $cm^{-1}$ | —$CH_3$, —$CH_2$ |
| 1377 $cm^{-1}$ | —$CH_3$ |
| 1743 $cm^{-1}$ | —CO—O— |
| 3430, 1076 $cm^{-1}$ | —CH—, —C—O— |
| 970, 920 $cm^{-1}$ | —C—N— |
| 722 $cm^{-1}$ | —$(CH_2)_n$—, high absorption |

The number of the protons of each substance was analyzed with $^1H$ NMR spectrum analysis as follows, and the above two reaction products were identified to be a diester derivative and a triester derivative.

Diester derivative ($C_{33}H_{66}O_7NCl$)

a (3H×2, 0.88 ppm), b (16H×2, 1.26 ppm), c (2H×2, 1.60 ppm), d (2H×2, 2.39 ppm), e (9H, 3.41 ppm), f (8H, 3.79–5.18 ppm)

Triester derivative ($C_{45}H_{88}O_8NCl$)

a (3H×3, 0.88 ppm), b (16H×3, 1.26 ppm), c (2H×3, 1.59 ppm), d (2H×3, 2.36 ppm), e (9H, 3.46 ppm), f (8H, 3.86–5.33 ppm)

Example 6

Determination of craft point, critical micelle concentration and surface tension
Testing Condition and Procedure An aqueous solution of 1 weight % of a surfactant (solution with pure water) was prepared and the craft point, at which a surfactant dissolves clearly, was determined with visual inspection. And the aqueous solution of several surfactants with varied concentration was prepared with pure water and their surface tension at 25° C. was determined.

The result is shown in Tables 1 and 2.

TABLE 1

| Reaction product | Craft point (1 wt %, ° C.) | Critical micelle concentration cmc (mol/liter) | Surface tension γ cmc (mN/m) |
|---|---|---|---|
| Monolaurate derivative | <0 | $1.2 \times 10^{-3}$ | 30.2 |
| Monomyristate derivative | <0 | $3.4 \times 10^{-4}$ | 34.2 |
| Monopalmitate derivative | 33.5 | | |
| Monostearate derivative | 40.5 | | |

TABLE 2

| Reaction product | Concentration (wt %) | (mol/liter) | Surface tension (mN/m) |
|---|---|---|---|
| Dilaurate derivative | 0.005 | $3 \times 10^{-5}$ | 27.0 |
| | 0.01 | $1.6 \times 10^{-4}$ | 27.0 |
| Trilaurate derivative | 0.0008 | $1 \times 10^{-5}$ | 48.0 |
| | 0.0024 | $3 \times 10^{-5}$ | 34.3 |
| Monopalmitate derivative | 0.1 | $2 \times 10^{-3}$ | 29.0 |

Biodegradability of Derivatives

The biodegradability of the derivatives was determined by checking the degree of degradation of those chemicals by microorganisms (procedures defined in Japanese domestic low for regulation of chemical substances and in OECD) with a degradation tester and closed system oxygen consumption meter. The test was continued for 14 days and the biodegradability data was calculated into percentage. The result is shown in Table 3.

TABLE 3

| Reaction product | Biodegradability (%) |
|---|---|
| Cetyl trimethyl ammonium bromide | -2.2 |
| Quaternary salt of methyl glucamine | 17.1 |
| Monolaurate | 43.0 |
| Dilaurate | 41.1 |
| Trilaurate | 47.3 |
| Monomyristate | 35.5 |
| Monopalmitate | 36.7 |
| Monostearate | 57.5 |

The 100-% degradability in the testing means that whole of a test sample has been degraded into inorganic substances such as carbon dioxide. As shown above, cetyl trimethyl ammonium bromide, one of popular cationic surfactants, exhibited minus biodegradability. That means the surfactant inhibited the propagation of activated sludge in addition to not being degraded by activated sludge. On the contrary, the cationic surfactants of the present invention exhibited superior biodegradability.

Example 7

Synthesis of monopalmitate

The trimethyl ammonium salt of N-methyl glucamine (an iodine compound) (3.64 mM) was dissolved in the mixture of 5 ml of piridine anhydride and 10 ml of DMF anhydride and the solution was cooled down to 5° C. Then palmitic acid chloride (3.64 mM) was added and the mixture was reacted at 5° C. for 3 hours. Approx. 30 ml of ethanol was added and agitated for 30 minutes at room temperature. Then the solvent in the reacted mixture was removed with a rotary evaporator under partial vacuum. The residue of the reaction was analyzed with TLC and the monoester generated in the reaction was quantitatively analyzed. The reaction product was refined with silica gel column chromatography for removing impurities, such as piridine chloride. The refined product was identified to be monopalmitate with the NMR spectrum.

Monolaurate was also produced and identified quantitatively in the case palmitic acid chloride was replaced by lauric acid chloride.

Example 8

The trimethyl ammonium salt of N-methyl glucamine (an iodine compound) (2.85 mM) was dissolved in the mixture of 4 ml of piridine anhydride and 10 ml of DMF anhydride and the solution was cooled down to 5° C. Then palmitic acid chloride (5.70 mM) was added and the mixture was reacted at 5° C. for 6 hours. Approx. 20 ml of ethanol was added and agitated for 30 minutes at room temperature. Then the solvent in the reacted mixture was removed with a rotary evaporator under partial vacuum. The residue of the reaction was analyzed with TLC and the bisester generated in the reaction was quantitatively analyzed. The reaction product was refined with silica gel column chromatography for removing impurities, such as piridine chloride. The refined product was identified to be bispalmitate with the NMR spectrum.

Bislaurate was also produced and identified quantitatively in the case palmitic acid chloride was replaced by lauric acid chloride.

Example 9

The trimethyl ammonium salt of N-methyl glucamine (an iodine compound) (15 mM) was dissolved in the mixture of 20 ml of piridine anhydride and 50 ml of DMF anhydride and the solution was cooled down to 5° C. Then lauric acid chloride (49.5 mM) was added and the mixture was reacted at 5° C. for 6 hours. Approx. 100 ml of ethanol was added and agitated for 30 minutes at room temperature. Then the solvent in the reacted mixture was removed with a rotary evaporator under partial vacuum. The residue of the reaction was analyzed with TLC and triester was found as the major product of the reaction. The reaction product was refined with silica gel column chromatography for removing impurities, such as piridine chloride. The refined product was identified to be trilaurate with the NMR spectrum.

Tripalmitate was also produced as a major product by replacing the lauric acid chloride with palmitic acid chloride. Tripalmitate could be refined by re-crystallizing out of ethanol solution not with refining with silica gel column chromatography.

Example 10

Three types of fabric samples were dipped in 1-liter of 0.005-wt % aqueous solution of each of $C_{12}$-monoester, $C_{12}$-bisester, $C_{16}$-monoester and $C_{16}$-bisester produced in Examples 7 and 8 and dimethyl dioctadecyl ammonium chloride (DSDMAC) simultaneously for 30 minutes. Then the fabric samples were taken out, softly squeezed and dried at room temperature. (10A) Determination of water-absorption effect (referred to JIS P-8141, Height of absorbed water).

The wetting of the fabric samples (2 cm and 10 cm oblong pieces) treated with the aqueous solution of the five surfactants mentioned above was tested with pure water in a solvent vessel for TLC analysis. The wetting was determined by measuring the height (cm) of the water penetrated and rose up the fabric samples out of the water surface. The height was represented by the average of the values from two times testing. The test was performed in a room of a fixed temperature and humidity (at 25° C. and 40% RH).

TABLE 4

| Reaction product | Cotton sheeting | Polyester/cotton blend (65:35, %) | Polyester taffeta |
| --- | --- | --- | --- |
| Not treated | 6.7 | 6.4 | 0.8 |
| $C_{12}$-monoester | 7.0 | 6.0 | 2.0 |
| $C_{12}$-bisester | 6.4 | 5.6 | 1.7 |
| $C_{16}$-monoester | 5.6 | 4.9 | 2.7 |
| $C_{16}$-bisester | 2.2 | 1.8 | 1.4 |
| DSDMAC | 3.9 | 3.7 | 0.8 |

(10B) Antistaticity Test

Testing device: Static Meter, S-4104III, by Nippon Static

Testing method: The treated fabric samples mentioned above were charged with 10-kV static electricity for 30 seconds. The charge dissipation with time was recorded on a chart, and the static half-life (sec) was calculated from the data on the chart for evaluation. The test was performed in a room of a fixed temperature and humidity (at 25° C. and 40% RH).

TABLE 5

| Reaction product | Cotton sheeting | Polyester/cotton blend (65:35, %) | Polyester taffeta |
| --- | --- | --- | --- |
| Not treated | 1.14 | 1.20 | 5.02 |
| $C_{12}$-monoester | 1.03 | 1.16 | 5.6 |
| $C_{12}$-bisester | 1.09 | 1.30 | 12.8 |
| $C_{16}$-monoester | 1.01 | 1.15 | 4.5 |
| $C_{16}$-bisester | 1.09 | 1.34 | 10.0 |
| DSDMAC | 0.96 | 1.35 | 12.9 |

(10C) Frictional Coefficient

Testing device: Surface friction meter, Type HEIDON-14D, by Shintoh Science Co., Ltd.

Testing condition: speed for pulling samples 300 mm/min, 300-g loading on piled two pieces of a fabric sample loaded in an area of a circle of 2.5 cm diameter. The treated fabric samples mentioned above were tested in a room of a fixed temperature and humidity (at 25° C. and 40% RH).

TABLE 6

| | Static frictional coefficient/Dynamic frictional coefficient | |
| --- | --- | --- |
| Reaction product | Cotton sheeting | Polyester/cotton blend (65:35%) |
| Not treated | 0.28/0.25 | 0.26/0.22 |
| $C_{12}$-monoester | 0.26/0.22 | 0.18/0.17 |
| $C_{12}$-bisester | 0.16/0.12 | 0.22/0.18 |
| $C_{16}$-monoester | 0.35/0.32 | 0.19/0.18 |
| $C_{16}$-bisester | 0.19/0.12 | 0.15/0.14 |
| DSDMAC | 0.13/0.07 | 0.19/0.18 |

Although the conventional development trend of cationic surfactants has been concentrated on the surfactants having a molecular structure in which esters are introduced into alkyl chains, it is more advantageous to develop compounds derived from natural sugars for meeting the current trend toward surfactants of higher biodegradability. The inventors of the present invention investigated on deriving cationic surfactants from the amine derivatives of reducing sugar of glucose or the amine derivatives of hexose alcohols that are reducing alcohol of hexose. And they found the developed compound produced through esterifying a quaternary salt of 1-amino-hexose alcohol with a fatty acid had superior biodegradability.

And the fabric treated with the cationic surfactants of the present invention exhibited superior water absorption and antistaticity, and low friction.

What is claimed is:

1. A cationic surfactant represented by the following formula (1)

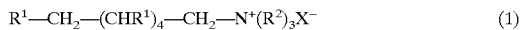

wherein the five $R^1$s are, independently of each other, hydroxyls or their esters, the three $R^2$s are, independently of each other, C1-6 hydrocarbons that can contain hydroxyls or esters, $X^-$ is an anion of halogens, hydrosulfate or organic acids, and at least one of the five $R^1$s is an ester.

2. A cationic surfactant represented by the following formula (1)

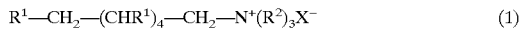

wherein the five $R^1$s are, independently of each other, hydroxyls or their esters, $X^-$ is an anion of halogens, hydrosulfate or organic acids, and at least one of the five $R^1$s is an ester, and the three $R^2$s are methyls.

3. A cationic surfactant represented by the following formula (1)

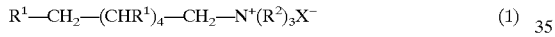

wherein the five $R^1$s are, independently of each other, hydroxyls or their esters, the three $R^2$s are, independently of each other, C1-6 hydrocarbons that can contain hydroxyls or esters, $X^-$ is an anion of halogens, hydrosulfate or organic acids, and at least one of the five $R^1$s is an ester, of which biodegradability with active sludge is 30% or more.

4. Fiber treated with one of the cationic surfactants of claims 1 to 3.

5. A process for producing a cationic surfactant of formula (1) as set forth in claim 1, comprising (A) reacting 1-amino hexose alcohol represented by formula (2):

with a halide compound of formula (3):

wherein $R^2$ and X are defined above in connection with formula (1), to produce an ammonium salt of N-hydrocarbon-1-amino hexose alcohol represent by formula (4):

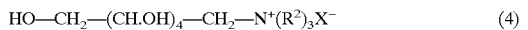

where $R^2$ and X are defined above in connection with formula (1), and (B) reacting the compound of formula (4) with acid halide.

6. A process for producing a cationic surfactant of formula (1) as set forth in claim 1, comprising (A) reacting 1-amino hexose alcohol represented by formula (2):

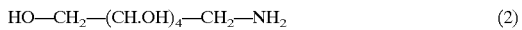

with a halide compound of formula (3):

wherein $R^2$ and X are defined above in connection with formula (1), to produce an ammonium salt of N-hydrocarbon-1-amino hexose alcohol represent by formula (4):

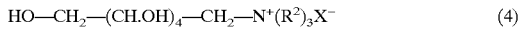

where $R^2$ and X are defined above in connection with formula (1), and (B') dehydrating and condensing the compound of formula (4) with organic acid.

7. A process for producing a cationic surfactant of formula (1) as set forth in claim 1, wherein in formula (1), one of the three $R^2$s is a methyl group and the other two are, independently, hydrocarbons which may contain hydroxyl or ester groups, comprising (A) reacting N-methyl glucamine represented by formula (5):

with a halide compound of formula (3):

wherein $R^2$ and X are defined above in connection with formula (1), to produce an ammonium salt of N-hydrocarbon-1-amino hexose alcohol represent by formula (4):

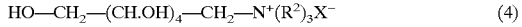

where $R^2$ and X are defined above in connection with formula (1), and (B") reacting the compound of formula (4) with acid halide.

8. The cationic surfactant according to claim 1, wherein the at least one ester represented by $R^1$ is an ester of the formula RCOO—, wherein R represents a hydrocarbon having from 5 to 28 carbon atoms.

9. The cationic surfactant according to claim 8, wherein only one of the groups $R^1$ is said ester.

10. The cationic surfactant according to claim 1, wherein at least two of the groups $R^1$ are said ester.

11. The cationic surfactant according to claim 1, which is at least one monoester represented by the formula

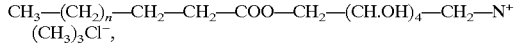

wherein n is a number of from 8 to 14.

12. Fiber according to claim 4, wherein the fiber contains from 0.005 to 3 weight percent of cationic surfactant, based on the weight of the fiber.

13. A hair-care composition comprising oil ingredient and cationic surfactant of formula (1) as set forth in any one of claims 1 to 3.

14. The hair-care composition according to claim 13, which comprises from 1 to 5% by weight of cationic surfactant.

* * * * *